US011071503B2

(12) United States Patent
Liu et al.

(10) Patent No.: US 11,071,503 B2
(45) Date of Patent: Jul. 27, 2021

(54) PHYSIOLOGICAL PARAMETER DISPLAY METHODS AND SYSTEMS

(71) Applicant: Shenzhen Mindray Bio-Medical Electronics Co., Ltd., Shenzhen (CN)

(72) Inventors: Zhonghua Liu, Shenzhen (CN); Guanglei Chen, Shenzhen (CN); Cong Xu, Shenzhen (CN); Hao Fang, Shenzhen (CN); Fangyong Guan, Shenzhen (CN); Yawei Sun, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 159 days.

(21) Appl. No.: 16/127,775

(22) Filed: Sep. 11, 2018

(65) Prior Publication Data
US 2019/0000400 A1 Jan. 3, 2019

Related U.S. Application Data

(63) Continuation of application No. PCT/CN2016/076429, filed on Mar. 15, 2016.

(51) Int. Cl.
*A61B 5/00* (2006.01)
*A61B 5/0245* (2006.01)
(Continued)

(52) U.S. Cl.
CPC ............ *A61B 5/742* (2013.01); *A61B 5/0006* (2013.01); *A61B 5/0205* (2013.01); *A61B 5/0245* (2013.01); *A61B 5/02405* (2013.01); *A61B 5/7275* (2013.01); *A61B 5/746* (2013.01); *G16H 40/63* (2018.01); *A61B 5/02438* (2013.01); *A61B 5/7465* (2013.01)

(58) Field of Classification Search
CPC ................................ A61B 5/742; A61B 5/746
See application file for complete search history.

(56) References Cited

U.S. PATENT DOCUMENTS

| 4,679,144 A | 7/1987 | Cox et al. |
| 6,579,231 B1 | 6/2003 | Phipps |

(Continued)

FOREIGN PATENT DOCUMENTS

| CN | 200977155 Y | 11/2007 |
| CN | 101742981 A | 6/2010 |

(Continued)

OTHER PUBLICATIONS

Sukuvaara et al., "Intelligent Patient Monitor—Its Functions and User Interface," Computer Science, Materials Science, 1991, pp. 373-376.

(Continued)

*Primary Examiner* — Michael J D Abreu
(74) *Attorney, Agent, or Firm* — Kory D. Christensen

(57) ABSTRACT

A physiological parameter display method may include: controlling the terminal to enter into one of multiple different working modes; obtaining a physiological parameter analysis result corresponding to the current working mode; and presenting corresponding output information according to the received physiological parameter analysis result, wherein the output information includes the received physiological parameter analysis result.

15 Claims, 8 Drawing Sheets

(51) Int. Cl.
    *A61B 5/024*         (2006.01)
    *G16H 40/63*        (2018.01)
    *A61B 5/0205*      (2006.01)

(56) References Cited

U.S. PATENT DOCUMENTS

| | | |
|---|---|---|
| 7,809,528 B2 | 10/2010 | Zeng et al. |
| 2008/0027679 A1 | 1/2008 | Shklarski |
| 2008/0082659 A1* | 4/2008 | Haslehurst ............ G16H 40/63 709/224 |
| 2008/0234592 A1 | 9/2008 | Lim et al. |

FOREIGN PATENT DOCUMENTS

| | | |
|---|---|---|
| CN | 102438507 A | 5/2012 |
| CN | 103230269 A | 8/2013 |
| WO | WO 2006076498 A2 | 7/2006 |
| WO | WO 2006076498 A3 | 7/2006 |

OTHER PUBLICATIONS

Extended European search report, Application No. 16893882.7, dated Nov. 4, 2019.

\* cited by examiner

PHYSIOLOGICAL PARAMETER DISPLAY METHODS AND SYSTEMS

CROSS-REFERENCE TO RELATED APPLICATIONS

This application is a continuation of PCT App. No. PCT/CN2016/076429, filed Mar. 15, 2016, for PHYSIOLOGICAL PARAMETER DISPLAY METHOD AND SYSTEM, PHYSIOLOGICAL PARAMETER PROCESSING METHOD AND SYSTEM, AND RELATED DEVICES, which is incorporated herein by reference.

TECHNICAL FIELD

The present disclosure relates to the field of medical monitoring and, in particular, to physiological parameter display methods and systems.

BACKGROUND

Electrocardiography requires electrodes to be placed with professional medical knowledge and requires interpretation of the resulting waveforms. Electrocardiography has been used in hospitals, but may not fully meet the requirements of clinical applications. For patients having chronic heart disease, or for healthy people who care about their heart function, how to display and track the results of electrocardiography, i.e., electrocardiograms, is a basic problem that needs to be solved if electrocardiography is to be used outside of a hospital environment.

With the rapid development of semiconductor and battery technologies, many wearable electrocardiography apparatuses have emerged, and this has solved the first problem of being used in home applications. However, effectively displaying data collected by a wearable electrocardiography device to achieve the real heart function management is an important technical problem that needs to be solved.

SUMMARY

One embodiment of the present disclosure includes a physiological parameter display method and system, a physiological parameter processing method and system, a terminal, and a server, which may effectively meet different requirements of the user under varying conditions, so that physical condition management effects may be effectively achieved.

One embodiment of the present disclosure includes a physiological parameter display method which is applied to a terminal, the terminal being capable of communicating with a server and a wireless sensor, respectively, the physiological parameter display method including: controlling the terminal to enter into one of multiple different working modes, the different working modes including at least a real-time parameter mode, a real-time monitoring mode, an event measurement mode, and a segment dynamic recording mode; acquiring a physiological parameter analysis result corresponding to a current working mode, wherein acquiring the physiological parameter analysis result in the real-time parameter mode includes the terminal processing the physiological parameter sensed by the wireless sensor at a current moment to acquire a first physiological parameter analysis result; acquiring the physiological parameter analysis result in the real-time monitoring mode includes the terminal processing the physiological parameter sensed by the wireless sensor in a successive time period starting from the current moment to acquire a second physiological parameter analysis result; acquiring the physiological parameter analysis result in the event measurement mode includes the terminal processing the physiological parameter sensed by the wireless sensor in a preset time period starting from the current moment to acquire a third physiological parameter analysis result; and acquiring the physiological parameter analysis result in the segment dynamic recording mode includes the terminal transmitting a first control instruction to the server in response to a first input from a user, so as to acquire, from the server, a fourth physiological parameter analysis result obtained by means of the server processing the physiological parameter in a first set time period, the first control instruction including a start time and an end time of the first set time period; and presenting corresponding output information according to the acquired physiological parameter analysis result, wherein the output information includes the acquired physiological parameter analysis result.

Acquiring the physiological parameter analysis result in the segment dynamic recording mode may further include the terminal transmitting a second control instruction to the wireless sensor in response to a second input from the user, so as to acquire the physiological parameter in the first set time period from the wireless sensor and to process the physiological parameter in the first set time period to acquire a fifth physiological parameter analysis result, a complexity of the fourth physiological parameter analysis result being greater than that of the fifth physiological parameter analysis result.

The different working modes further include a long-time big-data mode, wherein acquiring the physiological parameter analysis result in the long-time big-data mode is transmitting a third control instruction to the server, so as to acquire, from the server, a sixth physiological parameter analysis result obtained by means of the server processing the physiological parameter in a second set time period, the third control instruction including a start time and an end time of the second set time period, and a duration of the first set time period being shorter than that of the second set time period.

The first physiological parameter analysis result, the second physiological parameter analysis result, the third physiological parameter analysis result, the fourth physiological parameter analysis result, the fifth physiological parameter analysis result, and the sixth physiological parameter analysis result are different from one another.

Presenting the corresponding output information according to the second physiological parameter analysis result in the real-time monitoring mode may include: displaying the second physiological parameter analysis result; determining whether an abnormality has occurred according to the second physiological parameter analysis result; and displaying alarm information when the abnormality has occurred.

Presenting the corresponding output information according to the third physiological parameter analysis result in the event measurement mode may include: displaying the third physiological parameter analysis result; determining whether an abnormality has occurred according to the third physiological parameter analysis result; and displaying alarm information when the abnormality has occurred.

One embodiment of the present disclosure further discloses a physiological parameter processing method which is applied to a server, the server being capable of performing a communication connection with a terminal, the physiological parameter processing method including: receiving a control instruction transmitted by the terminal; processing a stored physiological parameter according to the control instruction to acquire a corresponding physiological parameter analysis result, wherein when the control instruction is to acquire an analysis result for the physiological parameter in a first set time period, the physiological parameter in the first set time period is processed to acquire a fourth physiological parameter analysis result; and when the control instruction is to acquire an analysis result for the physiological parameter in a second set time period, the physiological parameter in the second set time period is processed to acquire a sixth physiological parameter analysis result, a duration of the first set time period being shorter than that of the second set time period; and transmitting the physiological parameter analysis result to the terminal.

One embodiment of the present disclosure includes a physiological parameter display system which is applied to a terminal, the terminal being in communication connection with a server and/or a wireless sensor, the physiological parameter display system including: a working mode control unit for controlling the terminal to enter into one of multiple different working modes, the different working modes including at least a real-time parameter mode, a real-time monitoring mode, an event measurement mode, and a segment dynamic recording mode; a physiological parameter analysis result acquisition unit for acquiring a physiological parameter analysis result corresponding to a current working mode, wherein acquiring the physiological parameter analysis result in the real-time parameter mode includes the physiological parameter analysis result acquisition unit processing the physiological parameter sensed by the wireless sensor at a current moment to acquire a first physiological parameter analysis result; acquiring the physiological parameter analysis result in the real-time monitoring mode includes the physiological parameter analysis result acquisition unit processing the physiological parameter sensed by the wireless sensor in a successive time period starting from the current moment to acquire a second physiological parameter analysis result; acquiring the physiological parameter analysis result in the event measurement mode includes the physiological parameter analysis result acquisition unit processing the physiological parameter sensed by the wireless sensor in a preset time period starting from the current moment to acquire a third physiological parameter analysis result; and acquiring the physiological parameter analysis result in the segment dynamic recording mode includes the physiological parameter analysis result acquisition unit transmitting a first control instruction to the server in response to a first input from a user, so as to acquire, from the server, a fourth physiological parameter analysis result obtained by means of the server processing the physiological parameter in a first set time period, the first control instruction including a start time and an end time of the first set time period; and a display control unit for presenting corresponding output information according to the physiological parameter analysis result, wherein the output information includes the physiological parameter analysis result.

Acquiring the physiological parameter analysis result in the segment dynamic recording mode may further include the physiological parameter analysis result acquisition unit transmitting a second control instruction to the wireless sensor in response to a second input from the user, so as to acquire the physiological parameter in the first set time period from the wireless sensor and to process the physiological parameter in the first set time period to acquire a fifth physiological parameter analysis result, a complexity of the fourth physiological parameter analysis result being greater than that of the fifth physiological parameter analysis result.

The different working modes further include a long-time big-data mode, wherein acquiring the physiological parameter analysis result in the long-time big-data mode includes transmitting a third control instruction to the server, so as to acquire, from the server, a sixth physiological parameter analysis result obtained by means of the server processing the physiological parameter in a second set time period, the third control instruction including a start time and an end time of the second set time period, and a duration of the first set time period being shorter than that of the second set time period.

The first physiological parameter analysis result, the second physiological parameter analysis result, the third physiological parameter analysis result, the fourth physiological parameter analysis result, the fifth physiological parameter analysis result, and the sixth physiological parameter analysis result are different from one another.

The display control unit presenting the corresponding output information according to the second physiological parameter analysis result in the real-time monitoring mode may include: displaying the second physiological parameter analysis result; determining whether an abnormality has occurred according to the second physiological parameter analysis result; and displaying alarm information when the abnormality has occurred.

The display control unit presenting the corresponding output information according to the third physiological parameter analysis result in the event measurement mode may include: displaying the third physiological parameter analysis result; determining whether an abnormality has occurred according to the third physiological parameter analysis result; and displaying alarm information when the abnormality has occurred.

One embodiment of the present disclosure further includes a physiological parameter processing system which is applied to a server, wherein the server may be capable of performing a communication connection with a terminal, the physiological parameter processing system including: a receiving unit for receiving a control instruction transmitted by the terminal; an analysis processing unit for processing a stored physiological parameter according to the control instruction to acquire a corresponding physiological parameter analysis result, wherein when the control instruction is to acquire an analysis result for the physiological parameter in a first set time period, the physiological parameter in the first set time period is processed to acquire a fourth physiological parameter analysis result; and when the control instruction is to acquire an analysis result for the physiological parameter in a second set time period, the physiological parameter in the second set time period is processed to acquire a sixth physiological parameter analysis result, a duration of the first set time period being shorter than that of the second set time period; and a transmitting unit for transmitting the physiological parameter analysis result to the terminal.

One embodiment of the present disclosure further includes a terminal, including: a communication unit for performing a communication connection with a wireless sensor and a server respectively; a memory for storing program instructions; and a processor for executing the program instructions stored in the memory to execute the following operations: controlling the terminal to enter into one of multiple different working modes, the different working modes including at least a real-time parameter mode, a real-time monitoring mode, an event measurement mode, and a segment dynamic recording mode; acquiring a physiological parameter analysis result corresponding to a current working mode, wherein acquiring the physiological parameter analysis result in the real-time parameter mode includes the terminal processing the physiological parameter sensed by the wireless sensor at a current moment to acquire a first physiological parameter analysis result; acquiring the physiological parameter analysis result in the real-time monitoring mode includes the terminal processing the physiological parameter sensed by the wireless sensor in a successive time period starting from the current moment to acquire a second physiological parameter analysis result; acquiring the physiological parameter analysis result in the event measurement mode includes the terminal processing the physiological parameter sensed by the wireless sensor in a preset time period starting from the current moment to acquire a third physiological parameter analysis result; and acquiring the physiological parameter analysis result in the segment dynamic recording mode includes the terminal transmitting a first control instruction to the server in response to a first input from a user, so as to acquire, from the server, a fourth physiological parameter analysis result obtained by means of the server processing the physiological parameter in a first set time period, the first control instruction including a start time and an end time of the first set time period; and presenting corresponding output information according to the acquired physiological parameter analysis result, wherein the output information includes the acquired physiological parameter analysis result.

Acquiring the physiological parameter analysis result in the segment dynamic recording mode may further include the terminal transmitting a second control instruction to the wireless sensor in response to a second input from the user, so as to acquire the physiological parameter in the first set time period from the wireless sensor and to process the physiological parameter in the first set time period to acquire a fifth physiological parameter analysis result, a complexity of the fourth physiological parameter analysis result being greater than that of the fifth physiological parameter analysis result.

The different working modes further include a long-time big-data mode, wherein acquiring the physiological parameter analysis result in the long-time big-data mode is transmitting a third control instruction to the server, so as to acquire, from the server, a sixth physiological parameter analysis result obtained by means of the server processing the physiological parameter in a second set time period, the third control instruction including a start time and an end time of the second set time period, and a duration of the first set time period being shorter than that of the second set time period.

The first physiological parameter analysis result, the second physiological parameter analysis result, the third physiological parameter analysis result, the fourth physiological parameter analysis result, the fifth physiological parameter analysis result, and the sixth physiological parameter analysis result are different from one another.

Presenting the corresponding output information according to the second physiological parameter analysis result in the real-time monitoring mode may include: displaying the second physiological parameter analysis result; determining whether an abnormality has occurred according to the second physiological parameter analysis result; and displaying alarm information when the abnormality has occurred.

Presenting the corresponding output information according to the third physiological parameter analysis result in the event measurement mode may include: displaying the third physiological parameter analysis result; determining whether an abnormality has occurred according to the third physiological parameter analysis result; and displaying alarm information when the abnormality has occurred.

One embodiment of the present disclosure further discloses a server, including: a communication unit for performing a communication connection with a terminal; a memory for storing program instructions and at least one physiological parameter; and a processor for executing the program instructions stored in the memory to execute the following operations: receiving a control instruction transmitted by the terminal; processing a stored physiological parameter according to the control instruction to acquire a corresponding physiological parameter analysis result, wherein when it is interpreted that the control instruction is to acquire an analysis result for a physiological parameter in a first set time period, the physiological parameter in the first set time period is processed to acquire a fourth physiological parameter analysis result, and when it is interpreted that the control instruction is to acquire an analysis result for a physiological parameter in a second set time period, the physiological parameter in the second set time period is processed to acquire a sixth physiological parameter analysis result, a duration of the first set time period being shorter than that of the second set time period; and transmitting the physiological parameter analysis result to the terminal.

In the present disclosure, different working modes may be provided for a user to select, and corresponding physiological parameter analysis results may be displayed in the different working modes, and therefore different requirements of the user under different conditions may be effectively met, so that the physical condition management effect may be effectively achieved.

DETAILED DESCRIPTION

The technical solutions of the embodiments of the present application will be described below clearly and comprehensively in conjunction with the drawings of the embodiments of the present disclosure. The described embodiments are provided by example and not limitation. All other embodiments that would be obtained by those skilled in the art without expending inventive effort shall all fall within the scope of protection of the present disclosure.

Figure 1:
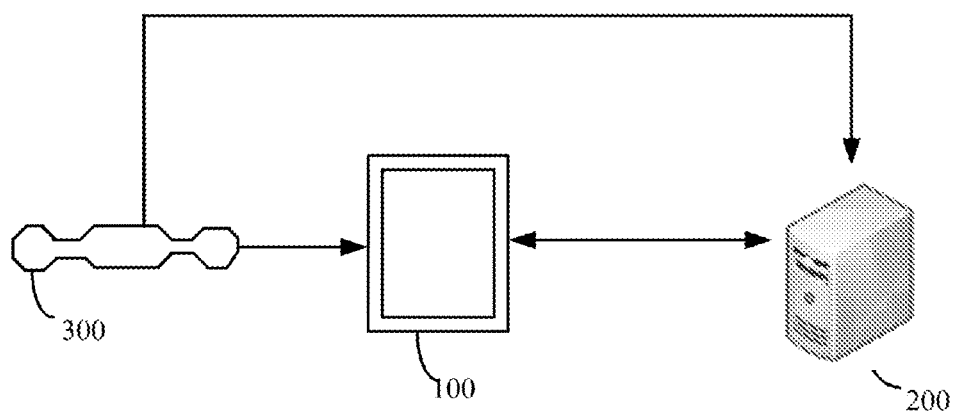
FIG. 1 is a schematic diagram of an application environment.

With reference to FIG. 1, an application environment in one embodiment of the present disclosure may include a terminal 100, a server 200, and a wireless sensor 300. The terminal 100 may be capable of initiating a communication connection with the server 200 and the wireless sensor 300 respectively, and generally, the terminal 100 may perform communication with the wireless sensor 300 by means of a short-distance communication protocol, such as the Bluetooth 4.0 low power protocol, the ZigBee protocol, and the ANT+ protocol and may perform the communication connection with the server 200 by means of optical fiber communication, Ethernet communication, 3G/4G communication, etc. The terminal 100 may be a smart phone, a tablet, a multimedia player, etc. The server 200 may be a server or a server cluster, and multiple servers may interact with one another. The wireless sensor 300 may be any sensor that is capable of sensing physiological parameters. For example, the sensed physiological parameter may be an electrocardiogram parameter, or a respiration rate, etc. The present disclosure describes the physiological parameter as the electrocardiogram parameter. The physiological parameter sensed by the wireless sensor 300 may be transmitted to the terminal 100, and then transmitted to the server 200 by the terminal 100, the server 200 analyzes the physiological parameter to obtain an analysis result, and the terminal 100 receives the analysis result from the server 200 for display, and the terminal 100 may also directly analyze the physiological parameter to obtain the analysis result. Generally, the analysis result obtained by the terminal 100 is simpler than the analysis result obtained by the server 200. Certainly, when the wireless sensor 300 is disconnected from the terminal 100, the wireless sensor 300 may first cache the sensed physiological parameter, and after the connection is recovered, the locally cached physiological parameter is transmitted to the terminal 100 and then transmitted to the server 200 by the terminal 100.

Figure 2:
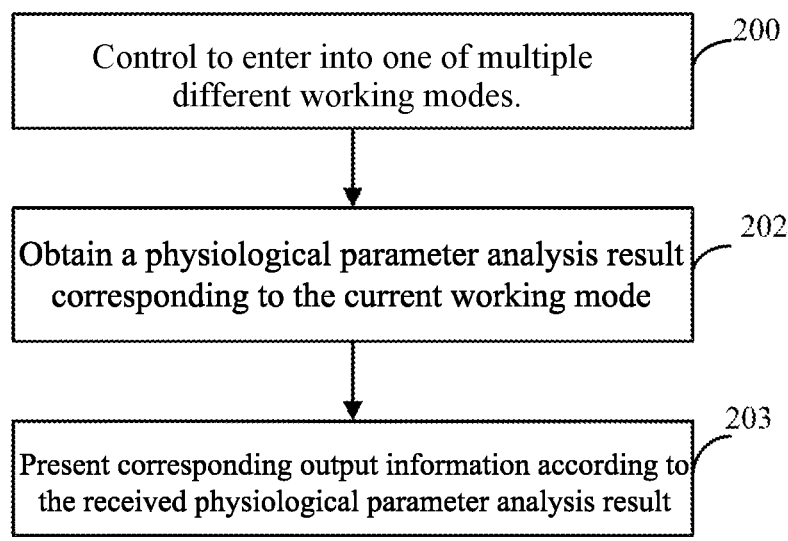
FIG. 2 is a flowchart of a physiological parameter display method.

With reference to FIG. 2, a physiological parameter display method in one embodiment of the present disclosure is applied to the terminal 100, and may include the steps of:

Step 200, controlling the terminal 100 to enter into one of multiple different working modes.

Figure 3:
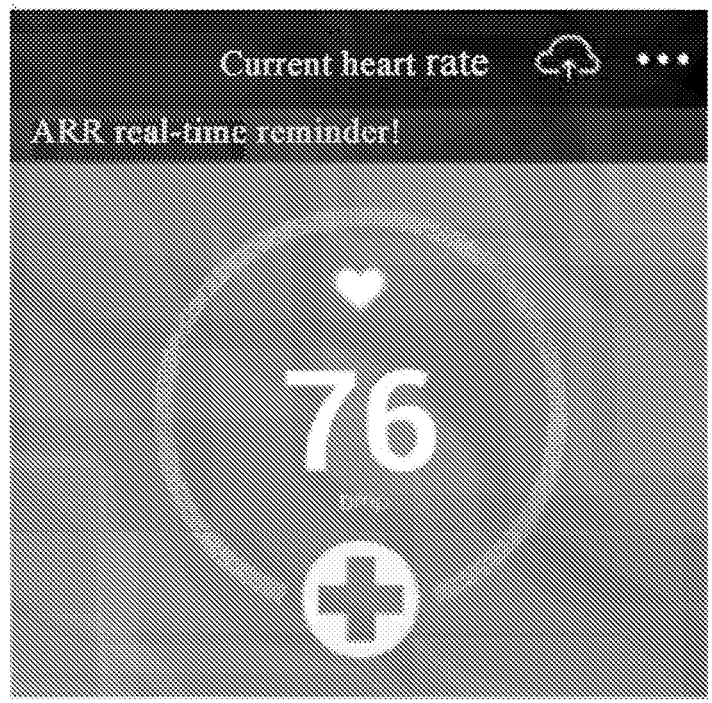
FIG. 3 is a schematic diagram of the content displayed by a terminal in a real-time parameter mode.
Figure 4:
FIG. 4 is a schematic diagram of the content displayed by a terminal in a real-time monitoring mode.
Figure 5:
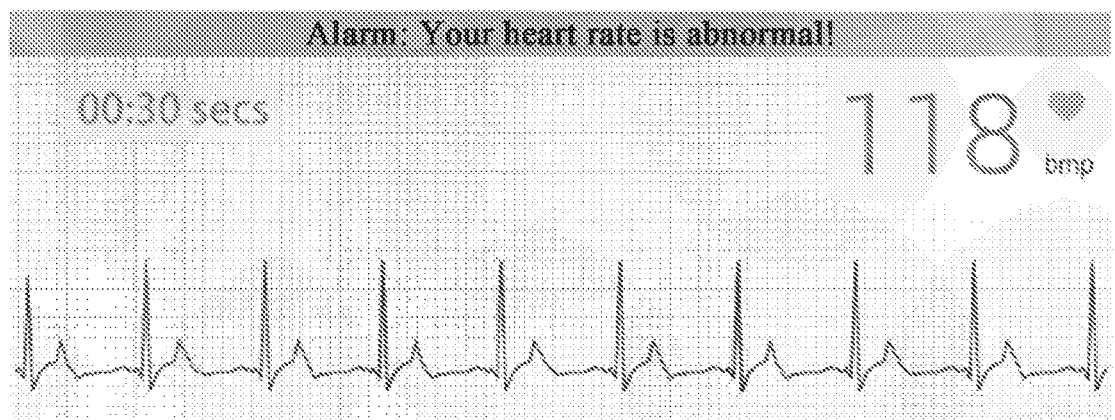
FIG. 5 is a schematic diagram of the content displayed by a terminal in an event measurement mode.
Figure 6:
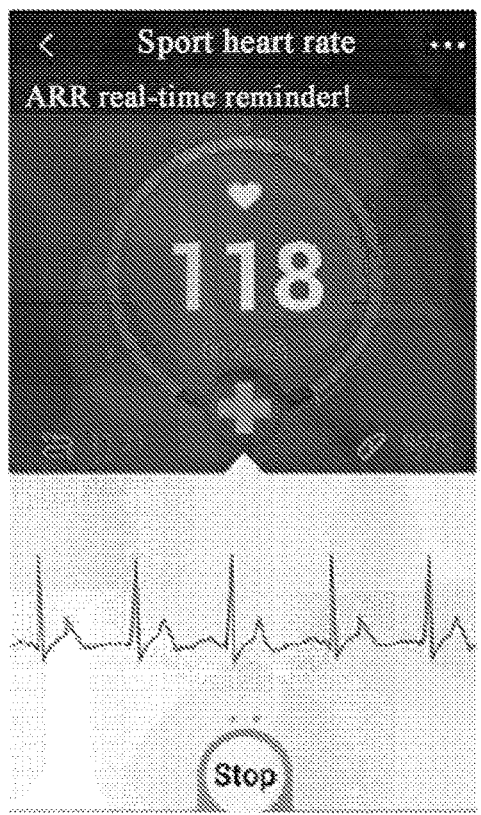
FIG. 6 is a schematic diagram of the content displayed by a terminal in a segment dynamic recording mode.

Specifically, the different working modes include at least a real-time parameter mode, a real-time monitoring mode, an event measurement mode, and a segment dynamic recording mode. The terminal 100 displays different information in the different working modes. In the real-time parameter mode, the terminal 100 displays a heart rate (as shown in FIG. 3) at the current moment, and it is suitable for a situation in which the current heart rate is desired. In the real-time monitoring mode, the terminal 100 displays an electrocardiogram waveform (as shown in FIG. 4) in real time which is used for real-time monitoring to observe whether there is an heart rate abnormality, or an arrhythmia abnormality, etc., and it is suitable for monitoring patients outside of the hospital. In the event measurement mode, the terminal 100 displays an electrocardiogram waveform (as shown in FIG. 5) for a time period (usually 30 S~60 S) starting from the current moment, so as to observe whether there is an abnormality, and it is suitable for the condition in which the user feels uncomfortable suddenly, for example, feels tightening of the chest. In the segment dynamic recording mode, the terminal 100 displays the electrocardiogram waveform analysis result (as shown in FIG. 6) for a specific time segment (for example, for a time period in which a certain sport is played), and it is suitable for the condition in which the user wants to know about the heart function when undertaking a certain activity, e.g., mountain climbing, swimming, etc. The detected and displayed contents in the real-time parameter mode, the real-time monitoring mode, and the event measurement mode are all related to the current physiological parameter of the user, and therefore before entering into the real-time parameter mode, the real-time monitoring mode, and the event measurement mode, it is necessary to ensure that the wireless sensor 300 is properly worn on the body of the user and is in a normal working state.

Figure 7:
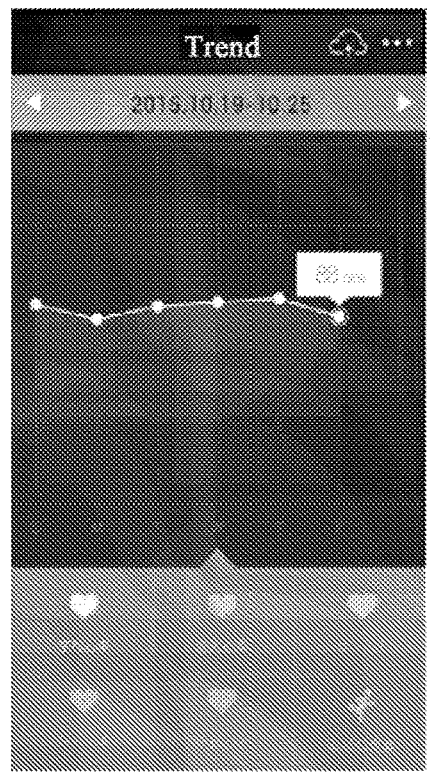
FIG. 7 is a schematic diagram of the content displayed by a terminal in a long-time big-data mode.

Further, the different working modes may further include a long-time big-data mode. In the long-time big-data mode, the terminal 100 displays a result (as shown in FIG. 7) obtained by analyzing dynamic record data for a time period exceeding a certain length (for example, several days, several months, etc.), e.g., a resting heart rate, the frequency of arrhythmias, etc., so as to observe a long-term changing trend of the heart function and to achieve the purpose of chronic disease management or heart function health management, wherein the record data analyzed in the long-time big-data mode contain all of the record data over a long time period.

Specifically, the switching of different working modes may be performed according to an input from the user. For example, initially, the terminal by default enters into the real-time parameter mode in which the user may select to enter into other modes according to different scenarios. For example, when the user suddenly feels a tight chest, he or she may select to enter into the event measurement mode. For another example, after swimming, the user wants to know about the heart function during swimming, he or she may select to enter into the segment dynamic recording mode and input a swimming time period (including a start time and an end time), then the server 200 processes and analyzes a received physiological parameter in the swimming time period to generate an electrocardiogram waveform analysis map, and the terminal 100 displays the generated electrocardiogram waveform analysis map, so that the user may learn about the heart function during swimming according to the displayed electrocardiogram waveform analysis map. As another example, several different working modes are initially provided for selection, and the user may select to enter into a required working mode according to different scenarios without using the real-time parameter mode as an entry for the other working modes. This embodiment does not limit the specific switching method for the different working modes. In one embodiment, when displaying the corresponding display content in each working mode, the terminal 100 further displays switching options for different modes, such as a mode switching icon, for the user to operate so as to generate input triggers to enter into the different modes.

Step 201, acquiring a physiological parameter analysis result corresponding to a current working mode.

Specifically, acquiring the physiological parameter analysis result in the real-time parameter mode is the terminal 100 processing a physiological parameter sensed by the wireless sensor 300 at the current moment to obtain a first physiological parameter analysis result. Acquiring the physiological parameter analysis result in the real-time monitoring mode includes the terminal 100 processing a physiological parameter sensed by the wireless sensor 300 in a successive time period starting from the current moment to obtain a second physiological parameter analysis result. Acquiring the physiological parameter analysis result in the event measurement mode is the terminal 100 processing a physiological parameter sensed by the wireless sensor 300 in a pre-set time period starting from the current moment to obtain a third physiological parameter analysis result. Acquiring the physiological parameter analysis result in the segment dynamic recording mode includes the terminal 100 transmitting a first control instruction to the server 200 in response to a first input from the user, so as to obtain, from the server 200, a fourth physiological parameter analysis result acquired by means of the server 200 processing a physiological parameter in a first set time period, the first control instruction including a start time and an end time of the first set time period. The first, second, third and fourth physiological parameter analysis results are different from one another. When the physiological parameter is the electrocardiogram parameter, the first, second, third and fourth physiological parameter analysis results are as described above with reference to FIGS. 3-6, and will not be described again.

Further, acquiring the physiological parameter analysis result in the segment dynamic recording mode may further include the terminal 100 transmitting a second control instruction to the wireless sensor 100 in response to a second input from the user, so as to acquire, from the wireless sensor 100, the physiological parameter in the first set time period, and to process the acquired physiological parameter to obtain a fifth physiological parameter analysis result. That is, in the segment dynamic recording mode, the terminal 100 may both obtain the corresponding physiological parameter analysis result by processing the physiological parameter in the first set time period by itself, and directly acquire the corresponding physiological parameter analysis result from the server 200. In the segment dynamic recording mode, an option may be provided for the user to select whether to acquire the corresponding physiological parameter analysis result from the server 200, or to obtain the corresponding physiological parameter analysis result through calculation by the terminal 100 itself. The fifth physiological parameter analysis result is usually simpler than the fourth physiological parameter analysis result.

Further, acquiring the physiological parameter analysis result in the long-time big-data mode is transmitting a third control instruction to the server 200, so as to acquire, from the server 200, a sixth physiological parameter analysis result acquired by means of the server 200 processing a physiological parameter in a second set time period, the third control instruction including a start time and an end time of the second set time period, and the sixth physiological parameter analysis result being different from the first, second, third, fourth and fifth physiological parameter analysis results. When the physiological parameter is the electrocardiogram parameter, the sixth physiological parameter analysis results is as described above with reference to FIG. 7, and will not be described again. The first set time period and the second set time period are set by the user via the terminal 100, wherein the duration of the first set time period is usually shorter than that of the second set time period, for example, the duration of the first set time period is usually from half an hour to 24 hours, and the duration of the second set time period is usually several days, several months, etc.

Step 202, presenting corresponding output information according to the acquired physiological parameter analysis result.

Specifically, the terminal 100 presenting the corresponding output information according to the acquired physiological parameter analysis result includes displaying the acquired physiological parameter analysis result.

In one embodiment, different working modes may be provided for a user to select, so as to display the corresponding physiological parameter analysis results in the different working modes, and therefore different requirements of the user under different conditions may be effectively met, so that the physical condition management effect may be effectively achieved.

In a further embodiment, presenting the corresponding output information according to the second physiological parameter analysis result when in the real-time monitoring mode may include:

displaying the second physiological parameter analysis result;

determining whether an abnormality has occurred according to the second physiological parameter analysis result; and displaying alarm information when the abnormality has occurred.

In this way, the user may intuitively determine whether there is an abnormality with the body according to whether the alarm information is displayed.

In a further embodiment, presenting the corresponding output information according to the third physiological parameter analysis result when in the event measurement mode may include:

displaying the third physiological parameter analysis result;

determining whether an abnormality has occurred according to the third physiological parameter analysis result; and displaying alarm information when the abnormality has occurred (as shown in FIG. 5).

In this way, the user may intuitively determine whether there is an abnormality with the body according to whether the alarm information is displayed.

Figure 8:
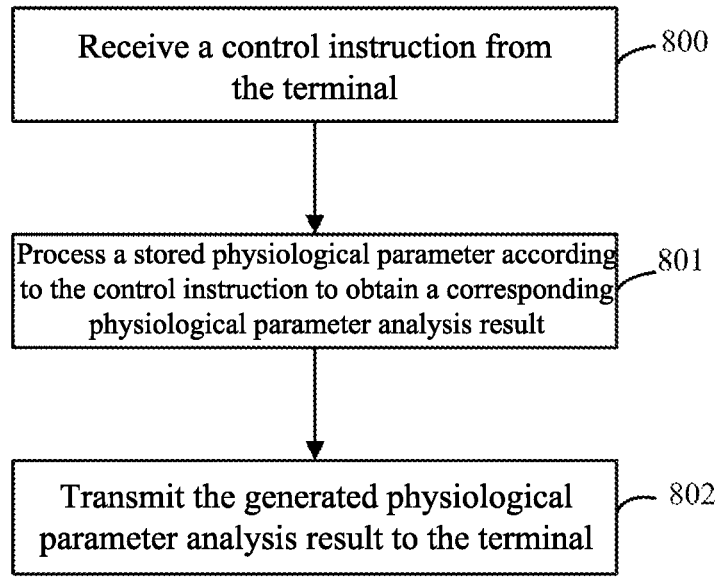
FIG. 8 is a flowchart of a physiological parameter processing method.

FIG. 8 is a flowchart of a physiological parameter processing method in one embodiment of the present disclosure, which is applied to the server 300, and may include the steps of:

Step 800, receiving a control instruction transmitted by the terminal 100.

Step 801, processing a stored physiological parameter according to the control instruction to obtain a corresponding physiological parameter analysis result.

Specifically, when it is interpreted that the control instruction is to acquire an analysis result for a physiological parameter in a first set time period, the physiological parameter in the first set time period is processed to obtain a fourth physiological parameter analysis result. When it is interpreted that the control instruction is to acquire an analysis result for a physiological parameter in a second set time period, the physiological parameter in the second set time period is processed to obtain a sixth physiological parameter analysis result, the duration of the first set time period being shorter than that of the second set time period, and the fourth physiological parameter analysis result being different from the sixth physiological parameter analysis result.

Step 802, transmitting the physiological parameter analysis result to the terminal 100.

Figure 9:
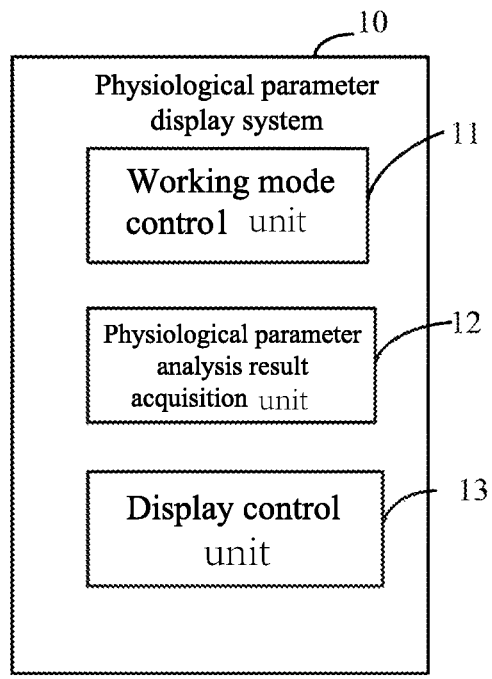
FIG. 9 is a functional unit diagram of a physiological parameter display system.

With reference to FIG. 9, a physiological parameter display system 10 in one embodiment of the present disclosure is applied to the terminal 100 and may include a working mode control unit 11, a physiological parameter analysis result acquisition unit 12, and a display control unit 13. The physiological parameter display system 10 may be an application that may be installed on the terminal 100 and has a login account, that is, a third-party application.

The working mode control unit 11 is used to control the terminal 100 to enter into one of multiple different working modes.

Specifically, the different working modes include at least a real-time parameter mode, a real-time monitoring mode, an event measurement mode, and a segment dynamic recording mode. The terminal 100 displays different information in the different working modes. In the real-time parameter mode, the terminal 100 displays a heart rate (as shown in FIG. 3) at the current moment, and it is suitable for a situation in which the current heart rate is desired. In the real-time monitoring mode, the terminal 100 displays an electrocardiogram waveform (as shown in FIG. 4) in real time which is used for real-time monitoring to observe whether there is an heart rate abnormality, or an arrhythmia abnormality, etc., and it is suitable for monitoring patients outside the hospital. In the event measurement mode, the terminal 100 displays an electrocardiogram waveform (as shown in FIG. 5) for a time period (usually 30 S~60 S) starting from the current moment, so as to observe whether there is an abnormality, and it is suitable for the condition in which the user feels uncomfortable suddenly, for example, feels a tight chest. In the segment dynamic recording mode, the terminal 100 displays the electrocardiogram waveform analysis result (as shown in FIG. 6) for a specific time segment (for example, for a time period in which a certain sport is played), and it is suitable for the condition in which the user wants to know about the heart function when undertaking a certain activity, e.g., mountain climbing, swimming, etc. The detected and displayed contents in the real-time parameter mode, the real-time monitoring mode, and the event measurement mode are all related to the current physiological parameter of the user, and therefore before entering into the real-time parameter mode, the real-time monitoring mode, and the event measurement mode, it is necessary to ensure that the wireless sensor 300 is properly worn on the body of the user and is in a normal working state.

Further, the different working modes may further include a long-time big-data mode. In the long-time big-data mode, the terminal 100 displays a result (as shown in FIG. 7) obtained by analyzing dynamic record data for a time period exceeding a certain length (for example, several days, several months, etc.), e.g., a resting heart rate, the frequency of arrhythmias, etc., so as to observe a long-term changing trend of the heart function and to achieve the purpose of chronic disease management or heart function health management, wherein the record data analyzed in the long-time big-data mode contain all of the record data over a long time period.

Specifically, the switching of different working modes may be performed according to an input from the user. For example, initially, the terminal by default enters into the real-time parameter mode in which the user may select to enter into other modes according to different scenarios. For example, when the user suddenly feels a tight chest, he or she may select to enter into the event measurement mode. For another example, after swimming, the user wants to know about the heart function during swimming, he or she may select to enter into the segment dynamic recording mode and input a swimming time period (including a start time and an end time), then the server 200 processes and analyzes a received physiological parameter in the swimming time period to generate an electrocardiogram waveform analysis map, and the terminal 100 displays the generated electrocardiogram waveform analysis map, so that the user may learn about the heart function during swimming according to the displayed electrocardiogram waveform analysis map. For another example, several different working modes are initially provided for selection, and the user may select to enter into a required working mode according to different scenarios without using the real-time parameter mode as an entry for the other working modes. This embodiment does not limit the specific switching method for the different working modes. In one embodiment, when displaying the corresponding display content in each working mode, the terminal 100 further displays switching options for different modes, such as a mode switching icon, for the user to operate so as to generate input triggers to enter into the different modes.

The physiological parameter analysis result acquisition unit 12 is used to acquire a physiological parameter analysis result corresponding to a current working mode.

Specifically, acquiring the physiological parameter analysis result in the real-time parameter mode is the physiological parameter analysis result acquisition unit 12 processing a physiological parameter sensed by the wireless sensor 300 at the current moment to obtain a first physiological parameter analysis result. Acquiring the physiological parameter analysis result in the real-time monitoring mode includes the physiological parameter analysis result acquisition unit 12 processing a physiological parameter sensed by the wireless sensor 300 in a successive time period starting from the current moment to obtain a second physiological parameter analysis result. Acquiring the physiological parameter analysis result in the event measurement mode is the physiological parameter analysis result acquisition unit 12 processing a physiological parameter sensed by the wireless sensor 300 in a pre-set time period starting from the current moment to obtain a third physiological parameter analysis result. Acquiring the physiological parameter analysis result in the segment dynamic recording mode is the physiological parameter analysis result acquisition unit 12 transmitting a first control instruction to the server 200 in response to a first input from the user, so as to obtain, from the server 200, a fourth physiological parameter analysis result acquired by means of the server 200 processing the physiological parameter in the first set time period, the first control instruction including a start time and an end time of the first set time period. The first, second, third and fourth physiological parameter analysis results are different from one another. When the physiological parameter is the electrocardiogram parameter, the first, second, third and fourth physiological parameter analysis results are as described above with reference to FIGS. 3-6, and will not be described again.

Further, acquiring the physiological parameter analysis result in the segment dynamic recording mode may further include the physiological parameter analysis result acquisition unit 12 transmitting a second control instruction to the wireless sensor 100 in response to a second input from the user, so as to acquire, from the wireless sensor 100, the physiological parameter in the first set time period, and to process the acquired physiological parameter to obtain a fifth physiological parameter analysis result. That is, in the segment dynamic recording mode, the terminal 100 may both obtain the corresponding physiological parameter analysis result by processing the physiological parameter in the first set time period by itself, and directly acquire the corresponding physiological parameter analysis result from the server 200. In the segment dynamic recording mode, an option may be provided for the user to select whether to acquire the corresponding physiological parameter analysis result from the server 200, or to obtain the corresponding physiological parameter analysis result through calculation by the terminal 100 itself. The fifth physiological parameter analysis result is usually simpler than the fourth physiological parameter analysis result.

Further, acquiring the physiological parameter analysis result in the long-time big-data mode is the physiological parameter analysis result acquisition unit 12 transmitting a third control instruction to the server 200, so as to acquire, from the server 200, a sixth physiological parameter analysis result acquired by means of the server 200 processing a physiological parameter in a second set time period, the third control instruction including a start time and an end time of the second set time period, and the sixth physiological parameter analysis result being different from the first, second, third, fourth and fifth physiological parameter analysis results. When the physiological parameter is the electrocardiogram parameter, the sixth physiological parameter analysis results is as described above with reference to FIG. 7, and will not be described again. The first set time period and the second set time period are set by the user via the terminal 100, wherein the duration of the first set time period is usually shorter than that of the second set time period, for example, the duration of the first set time period is usually from half an hour to 24 hours, and the duration of the second set time period is usually several days, several months, etc.

The display control unit 13 is used to present corresponding output information according to the acquired physiological parameter analysis result. Specifically, the display control unit 13 presenting the corresponding output information according to the acquired physiological parameter analysis result includes displaying the received physiological parameter analysis result.

In one embodiment, different working modes may be provided for a user to select, so as to display the corresponding physiological parameter analysis results in the different working modes, and therefore different requirements of the user under different conditions may be effectively met, so that the physical condition management effect may be effectively achieved.

In one further embodiment, the display control unit 13 presenting the corresponding output information according to the second physiological parameter analysis result when in the real-time monitoring mode may include:

displaying the second physiological parameter analysis result;

determining whether an abnormality has occurred according to the second physiological parameter analysis result; and displaying alarm information when the abnormality has occurred.

In this way, the user may intuitively determine whether there is an abnormality with the body according to whether the alarm information is displayed.

In one further embodiment, the display control unit 13 presenting the corresponding output information according to the third physiological parameter analysis result when in the event measurement mode may include:

displaying the third physiological parameter analysis result;

determining whether an abnormality has occurred according to the third physiological parameter analysis result; and displaying alarm information when the abnormality has occurred.

In this way, the user may intuitively determine whether there is an abnormality with the body according to whether the alarm information is displayed.

Figure 10:
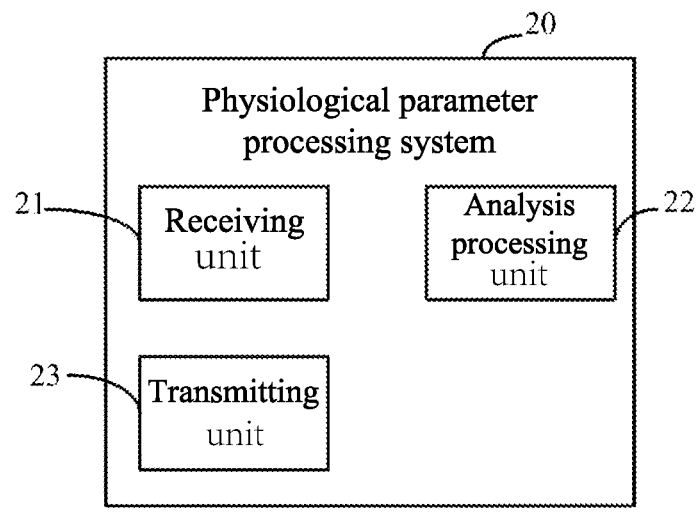
FIG. 10 is a functional unit diagram of a physiological parameter processing system.

With reference to FIG. 10, a physiological parameter processing system 20 in one embodiment of the present disclosure is applied to the server 200 and may include a receiving unit 21, an analysis processing unit 22, and a transmitting unit 23. The physiological parameter processing system 20 may be a background portion of the application (the physiological parameter display system 10) installed on the terminal 100.

The receiving unit 21 is used to receive the control instruction from the terminal 100.

The analysis processing unit 22 is used to process a stored physiological parameter according to the control instruction to obtain a corresponding physiological parameter analysis result.

Specifically, when it is interpreted that the control instruction is to acquire an analysis result for a physiological parameter in a first set time period, the physiological parameter in the first set time period is processed to obtain a fourth physiological parameter analysis result. When it is interpreted that the control instruction is to acquire an analysis result for a physiological parameter in a second set time period, the physiological parameter in the second set time period is processed to obtain a sixth physiological parameter analysis result, the duration of the first set time period being shorter than that of the second set time period, and the fourth physiological parameter analysis result being different from the sixth physiological parameter analysis result.

The transmitting unit 23 is used to transmit the generated physiological parameter analysis result to the terminal 100.

Figure 11:
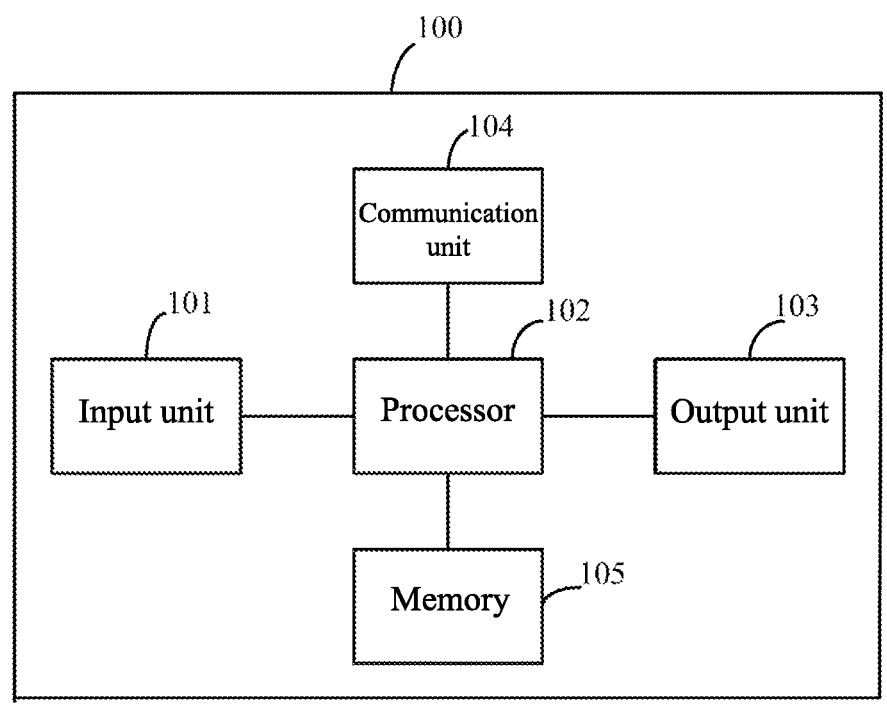
FIG. 11 is a schematic diagram of the basic structural of a terminal.

With reference to FIG. 11, the terminal 100 in one embodiments of the present disclosure may include components, such as an input unit 101, a processor 102, an output unit 103, a communication unit 104, and a memory 105. These components communicate over one or more buses. It is to be understood by those skilled in the art that the structure of the terminal 100 shown in FIG. 11 does not constitute a limit of the present disclosure, and it may be a bus-shaped structure or may be a star-shaped structure, and may also include more or fewer components than those shown in FIG. 11, or the combination of some components, or different component arrangements.

The input unit 101 is used to realize the interaction between the user and the terminal 100 and/or input of information to the terminal. For example, the input unit 101 may receive numeric or character information input by the user to generate a signal input related to user settings or function control. In the specific embodiments of the present disclosure, the input unit 101 may be a touch panel, or may be other human-machine interaction interfaces, such as physical input keys, a microphone, etc., and may also be other external information capturing devices, such as cameras.

The processor 102 is a control center of the terminal 100, which connects various parts of the entire terminal 100 using various interfaces and lines, and by running or executing program instructions and/or units stored in the memory 105 and executing instructions stored in the memory 105, executes various functions of the terminal 100 and/or processes the data. The processor 102 may be composed of an integrated circuit (IC), for example, may be composed of a single packaged IC, or may be composed by connecting multiple packaged ICs with the same function or different functions. For example, the processor 102 may include only a central processing unit (CPU), or may be a CPU, a digital signal processor (DSP), a graphics processing unit (GPU) and a combination of control chips (e.g., baseband chips) in the communication unit. In one embodiments of the present disclosure, the CPU may be a single operation core, and may also include multiple operation cores.

The output unit 103 may include, but is not limited to, an image output unit, a sound output and tactile output unit. The image output unit is used to output text, pictures, and/or videos. The image output unit may include a display panel, such as a display panel configured in the form of an LCD (Liquid Crystal Display), an OLED (Organic Light-Emitting Diode), or a field emission display (FED), etc. The image output unit may include a reflective display, for example, an electrophoretic display, or a display using interferometric modulation of light.

The memory 105 may be used to store program instructions and units, and the processor 102 executes various functional applications of the terminal 100 and realizes data processing by running the program instructions and units stored in the memory 105. The memory 105 mainly includes a program storage area and a data storage area, wherein the program storage area may store an operating system, program instructions required for at least one function, such as program instructions for performing physiological parameter display; and the data storage area may store data created according to the use of the terminal 100, such as the physiological parameter, etc. In the specific embodiments of the present disclosure, the memory 105 may include a volatile memory, such as a nonvolatile random access memory (NVRAM), a phase change RAM (PRAM), and a magnetoresistive RAM (MRAM), or may include a non-volatile memory, such as at least one magnetic disk storage device, an electrically erasable programmable read-only memory (EEPROM), and a flash memory device, e.g., a NOR flash memory or a NAND flash memory. The non-volatile memory stores the operating system and the program instructions executed by the processor unit.

The communication unit 104 is used to establish communication channels, so that the terminal 100 is connected to the server 200 and the wireless sensor 300 via the communication channels. The communication unit 104 may include wireless communication units such as a wireless local area network (wireless LAN) unit, a Bluetooth unit, a near field communication (NFC), a baseband unit, and wired communication units such as an Ethernet, a universal serial bus (USB), Lightning (currently used by Apple for iPhone apparatuses, etc.).

In the terminal 100 shown in FIG. 11, the processor 102 may call the program instructions stored in the memory 105 for executing the following operations:

controlling the terminal 100 to enter into one of multiple different working modes, wherein the multiple different working modes include at least a real-time parameter mode, a real-time monitoring mode, an event measurement mode, and a segment dynamic recording mode;

acquiring a physiological parameter analysis result corresponding to a current working mode, wherein acquiring the physiological parameter analysis result in the real-time parameter mode is the terminal 100 processing a physiological parameter sensed by the wireless sensor 300 at a current moment to acquire a first physiological parameter analysis result; acquiring the physiological parameter analysis result in the real-time monitoring mode is the terminal 100 processing a physiological parameter sensed by the wireless sensor 300 in a successive time period starting from the current moment to acquire a second physiological parameter analysis result; acquiring the physiological parameter analysis result in the event measurement mode is the terminal 100 processing a physiological parameter sensed by the wireless sensor 300 in a preset time period starting from the current moment to acquire a third physiological parameter analysis result; and acquiring the physiological parameter analysis result in the segment dynamic recording mode includes the terminal 100 transmitting a first control instruction to the server 200 in response to a first input from a user, so as to acquire, from the server 200, a fourth physiological parameter analysis result acquired by means of the server 200 processing a physiological parameter in a first set time period, the first control instruction including a start time and an end time of the first set time period; and presenting corresponding output information according to the received physiological parameter analysis result, wherein the output information includes the received physiological parameter analysis result.

Further, acquiring the physiological parameter analysis result in the segment dynamic recording mode may further include the terminal 100 transmitting a second control instruction to the wireless sensor 100 in response to a second input from the user, so as to acquire, from the wireless sensor 100, the physiological parameter in the first set time period, and to process the acquired physiological parameter to obtain a fifth physiological parameter analysis result, a complexity of the fourth physiological parameter analysis result being greater than that of the fifth physiological parameter analysis result.

Further, the different working modes may further include a long-time big-data mode, wherein acquiring the physiological parameter analysis result in the long-time big-data mode is transmitting a second control instruction to the server 200, so as to acquire, from the server 200, a sixth physiological parameter analysis result acquired by means of the server 200 processing a physiological parameter in a second set time period, the second control instruction including a start time and an end time of the second set time period, and a duration of the first set time period being shorter than that of the second set time period.

The first, second, third, fourth, fifth and sixth physiological parameter analysis results are different from one another.

In one embodiment, different working modes may be provided for a user to select, so as to display the corresponding physiological parameter analysis results in the different working modes, and therefore different requirements of the user under different conditions may be effectively met, so that the physical condition management effect may be effectively achieved.

In one further embodiment, presenting the corresponding output information according to the second physiological parameter analysis result when in the real-time monitoring mode may include:

displaying the second physiological parameter analysis result;

determining whether an abnormality has occurred according to the second physiological parameter analysis result; and displaying alarm information when the abnormality has occurred.

In this way, the user may intuitively determine whether there is an abnormality with the body according to whether the alarm information is displayed.

In one further embodiment, presenting the corresponding output information according to the third physiological parameter analysis result when in the event measurement mode may include:

displaying the third physiological parameter analysis result;

determining whether an abnormality has occurred according to the third physiological parameter analysis result; and displaying alarm information when the abnormality has occurred.

In this way, the user may intuitively determine whether there is an abnormality with the body according to whether the alarm information is displayed.

Figure 12:
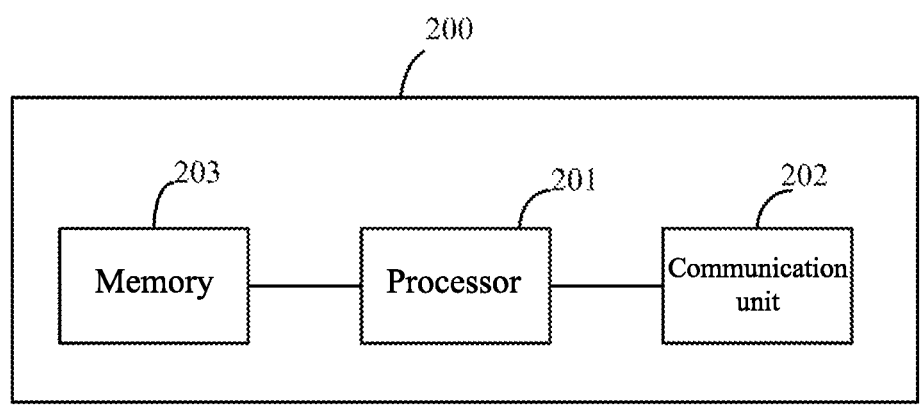
FIG. 12 is a schematic diagram of the basic structural of a server.

With reference to FIG. 12, the server 200 in one embodiments of the present disclosure may include components, such as a processor 201, a communication unit 202, and a memory 203. These components communicate over one or more buses. It is to be understood by those skilled in the art that the structure of the server 200 shown in FIG. 12 does not constitute a limit of the present disclosure, which may be a bus-shaped structure or may be a star-shaped structure, and may also include more or fewer components than those shown in FIG. 12, or the combination of certain components, or different component arrangements.

The processor 201 is a control center of the server 200, which connects various parts of the entire server 200 using various interfaces and lines, and by running or executing program instructions and/or units stored in the memory 203 and executing instructions stored in the memory 203, executes various functions of the server 200 and/or processes the data.

The memory 203 may be used to store program instructions and units, and the processor 201 executes various functional applications of the server 200 and realizes data processing by running the program instructions and units stored in the memory 203. The memory 203 mainly includes a program storage area and a data storage area, wherein the program storage area may store an operating system, program instructions required for at least one function, such as program instructions for performing physiological parameter processing; and the data storage area may store data created according to the use of the server, such as the physiological parameter.

The communication unit 202 is used to establish a communication channel, so that the server 200 is connected to the terminal 100 via the communication channel.

In the server 200 shown in FIG. 12, the processor 201 may call the program instructions stored in the memory 203 for executing the following operations:

receiving the control instruction from the terminal 100;

processing a stored physiological parameter according to the control instruction to acquire a corresponding physiological parameter analysis result, wherein when it is interpreted that the control instruction is to acquire an analysis result for a physiological parameter in a first set time period, the physiological parameter in the first set time period is processed to obtain a fourth physiological parameter analysis result; and when it is interpreted that the control instruction is to acquire an analysis result for a physiological parameter in a second set time period, the physiological parameter in the second set time period is processed to obtain a sixth physiological parameter analysis result, the duration of the first set time period being shorter than that of the second set time period, and the fourth physiological parameter analysis result being different from the sixth physiological parameter analysis result; and transmitting the generated physiological parameter analysis result to the terminal 100.

Described above are preferred embodiments of the present disclosure, and it should be noted that a person of ordinary skill in the art could also make some improvements and modifications without departing from the principles of the present disclosure and these improvements and modifications would all fall within the scope of protection of the present disclosure.

What is claimed is:

1. A physiological parameter display method which is applied to a terminal, the terminal is capable of communicating with a server and a wireless sensor respectively, the physiological parameter display method comprising:

displaying at least one switching option for a user to operate, so as to generate an input trigger to control the terminal to enter into one of multiple different working modes, the different working modes comprising at least a real-time parameter mode, a real-time monitoring mode, an event measurement mode, and a segment dynamic recording mode;

acquiring a physiological parameter analysis result corresponding to a current working mode, wherein acquiring the physiological parameter analysis result in the real-time parameter mode comprises the terminal processing the physiological parameter sensed by the wireless sensor at a current moment to acquire a first physiological parameter analysis result; acquiring the physiological parameter analysis result in the real-time monitoring mode comprises the terminal processing the physiological parameter sensed by the wireless sensor in a successive time period starting from a current moment to acquire a second physiological parameter analysis result; acquiring the physiological parameter analysis result in the event measurement mode comprises the terminal processing the physiological parameter sensed by the wireless sensor in a preset time period starting from a current moment to acquire a third physiological parameter analysis result; and acquiring the physiological parameter analysis result in the segment dynamic recording mode comprises the terminal transmitting a first control instruction to the server in response to a first input from a user, so as to acquire, from the server, a fourth physiological parameter analysis result obtained by means of the server processing the physiological parameter in a first set time period, the first control instruction comprising a start time and an end time of the first set time period, wherein acquiring the physiological parameter analysis result in the segment dynamic recording mode further comprises the terminal transmitting a second control instruction to the wireless sensor in response to a second input from the user, so as to acquire the physiological parameter in the first set time period from the wireless sensor, and processing the physiological parameter in the first set time period to acquire a fifth physiological parameter analysis result, a complexity of the fourth physiological parameter analysis result being greater than that of the fifth physiological parameter analysis result wherein, in the segment dynamic recording mode, an option is provided for the user to select whether to acquire the fourth physiological parameter analysis result from the server or to acquire the fifth physiological parameter analysis result from the terminal; and presenting corresponding output information on the terminal according to the acquired physiological parameter analysis result, wherein the output information comprises the acquired physiological parameter analysis result.

2. The physiological parameter display method of claim 1, wherein the different working modes further comprise a long-time big-data mode, wherein acquiring the physiological parameter analysis result in the long-time big-data mode comprises the terminal transmitting a third control instruction to the server, so as to acquire, from the server, a sixth physiological parameter analysis result obtained by means of the server processing the physiological parameter in a second set time period, the third control instruction comprising a start time and an end time of the second set time period, and a duration of the first set time period being shorter than that of the second set time period.

3. The physiological parameter display method of claim 2, wherein the first physiological parameter analysis result, the second physiological parameter analysis result, the third physiological parameter analysis result, the fourth physiological parameter analysis result, the fifth physiological parameter analysis result, and the sixth physiological parameter analysis result are different from one another.

4. The physiological parameter display method of claim 1, wherein presenting the corresponding output information according to the second physiological parameter analysis result in the real-time monitoring mode comprises:
displaying the second physiological parameter analysis result;
determining whether an abnormality has occurred according to the second physiological parameter analysis result; and
displaying alarm information when the abnormality has occurred.

5. The physiological parameter display method of claim 1, wherein presenting the corresponding output information according to the third physiological parameter analysis result in the event measurement mode comprises:
displaying the third physiological parameter analysis result;
determining whether an abnormality has occurred according to the third physiological parameter analysis result; and
displaying alarm information when the abnormality has occurred.

6. A physiological parameter display system which is applied to a terminal, the terminal is in communication connection with a server and/or a wireless sensor, the physiological parameter display system comprising:
a working mode control unit for displaying at least one switching option for a user to operate, so as to generate an input trigger to control the terminal to enter into one of multiple different working modes, the different working modes comprising at least a real-time parameter mode, a real-time monitoring mode, an event measurement mode, and a segment dynamic recording mode;
a physiological parameter analysis result acquisition unit for acquiring a physiological parameter analysis result corresponding to a current working mode, wherein acquiring the physiological parameter analysis result in the real-time parameter mode comprises the physiological parameter analysis result acquisition unit processing the physiological parameter sensed by the wireless sensor at a current moment to acquire a first physiological parameter analysis result; acquiring the physiological parameter analysis result in the real-time monitoring mode comprises the physiological parameter analysis result acquisition unit processing the physiological parameter sensed by the wireless sensor in a successive time period starting from a current moment to acquire a second physiological parameter analysis result; acquiring the physiological parameter analysis result in the event measurement mode comprises the physiological parameter analysis result acquisition unit processing the physiological parameter sensed by the wireless sensor in a preset time period starting from a current moment to acquire a third physiological parameter analysis result; and
acquiring the physiological parameter analysis result in the segment dynamic recording mode comprises the physiological parameter analysis result acquisition unit transmitting a first control instruction to the server in response to a first input from a user, so as to acquire, from the server, a fourth physiological parameter analysis result obtained by means of the server processing the physiological parameter in a first set time period, the first control instruction comprising a start time and an end time of the first set time period, wherein acquiring the physiological parameter analysis result in the segment dynamic recording mode further comprises the physiological parameter analysis result acquisition unit transmitting a second control instruction to the wireless sensor in response to a second input from the user, so as to acquire the physiological parameter in the first set time period from the wireless sensor, and processing the physiological parameter in the first set time period to acquire a fifth physiological parameter analysis result, a complexity of the fourth physiological parameter analysis result being greater than that of the fifth physiological parameter analysis result wherein, in the segment dynamic recording mode, an option is provided for the user to select whether to acquire the fourth physiological parameter analysis result from the server or to acquire the fifth physiological parameter analysis result from the terminal; and
a display control unit for presenting corresponding output information on the terminal according to the physiological parameter analysis result, wherein the output information comprises the physiological parameter analysis result.

7. The physiological parameter display system of claim 6, wherein the different working modes further comprise a long-time big-data mode, wherein acquiring the physiological parameter analysis result in the long-time big-data mode comprises the terminal transmitting a third control instruction to the server, so as to acquire, from the server, a sixth physiological parameter analysis result obtained by means of the server processing the physiological parameter in a second set time period, the third control instruction comprising a start time and an end time of the second set time period, and a duration of the first set time period being shorter than that of the second set time period.

8. The physiological parameter display system of claim 7, wherein the first physiological parameter analysis result, the second physiological parameter analysis result, the third physiological parameter analysis result, the fourth physiological parameter analysis result, the fifth physiological parameter analysis result, and the sixth physiological parameter analysis result are different from one another.

9. The physiological parameter display system of claim 6, wherein the display control unit presenting the corresponding output information according to the second physiological parameter analysis result in the real-time monitoring mode comprises:
displaying the second physiological parameter analysis result;
determining whether an abnormality has occurred according to the second physiological parameter analysis result; and
displaying alarm information when the abnormality has occurred.

10. The physiological parameter display system of claim 6, wherein the display control unit presenting the corresponding output information according to the third physiological parameter analysis result in the event measurement mode comprises:
displaying the third physiological parameter analysis result;
determining whether an abnormality has occurred according to the third physiological parameter analysis result; and
displaying alarm information when the abnormality has occurred.

11. A terminal, comprising:
a communication unit for performing a communication connection with a wireless sensor and/or a server respectively;
a memory for storing program instructions; and
a processor for executing the program instructions stored in the memory to execute the following operations:
displaying at least one switching option for a user to operate, so as to generate an input trigger to control the terminal to enter into one of multiple different working modes, the different working modes comprising at least a real-time parameter mode, a real-time monitoring mode, an event measurement mode, and a segment dynamic recording mode;
acquiring a physiological parameter analysis result corresponding to a current working mode, wherein acquiring the physiological parameter analysis result in the real-time parameter mode comprises the terminal processing the physiological parameter sensed by the wireless sensor at a current moment to acquire a first physiological parameter analysis result; acquiring the physiological parameter analysis result in the real-time monitoring mode comprises the terminal processing the physiological parameter sensed by the wireless sensor in a successive time period starting from a current moment to acquire a second physiological parameter analysis result; acquiring the physiological parameter analysis result in the event measurement mode comprises the terminal processing the physiological parameter sensed by the wireless sensor in a preset time period starting from a current moment to acquire a third physiological parameter analysis result; and
acquiring the physiological parameter analysis result in the segment dynamic recording mode comprises the terminal transmitting a first control instruction to the server in response to a first input from a user, so as to acquire, from the server, a fourth physiological parameter analysis result obtained by means of the server processing the physiological parameter in a first set time period, the first control instruction comprising a start time and an end time of the first set time period, wherein acquiring the physiological parameter analysis result in the segment dynamic recording mode further comprises the terminal transmitting a second control instruction to the wireless sensor in response to a second input from the user, so as to acquire the physiological parameter in the first set time period from the wireless sensor, and processing the physiological parameter in the first set time period to acquire a fifth physiological parameter analysis result, a complexity of the fourth physiological parameter analysis result being greater than that of the fifth physiological parameter analysis result; wherein, in the segment dynamic recording mode, an option is provided for the user to select whether to acquire the fourth physiological parameter analysis result from the server or to acquire the fifth physiological parameter analysis result from the terminal; and
presenting corresponding output information on the terminal according to the acquired physiological parameter analysis result, wherein the output information comprises the acquired physiological parameter analysis result.

12. The terminal of claim 11, wherein the different working modes further comprise a long-time big-data mode, wherein acquiring the physiological parameter analysis result in the long-time big-data mode comprises transmitting a third control instruction to the server, so as to acquire, from the server, a sixth physiological parameter analysis result obtained by means of the server processing the physiological parameter in a second set time period, the third control instruction comprising a start time and an end time of the second set time period, and a duration of the first set time period being shorter than that of the second set time period.

13. The terminal of claim 12, wherein the first physiological parameter analysis result, the second physiological parameter analysis result, the third physiological parameter analysis result, the fourth physiological parameter analysis result, the fifth physiological parameter analysis result, and the sixth physiological parameter analysis result are different from one another.

14. The terminal of claim 11, wherein presenting the corresponding output information according to the second physiological parameter analysis result in the real-time monitoring mode comprises:
displaying the second physiological parameter analysis result;
determining whether an abnormality has occurred according to the second physiological parameter analysis result; and
displaying alarm information when the abnormality has occurred.

15. The terminal of claim 11, wherein presenting the corresponding output information according to the third physiological parameter analysis result in the event measurement mode comprises:
displaying the third physiological parameter analysis result;
determining whether an abnormality has occurred according to the third physiological parameter analysis result; and
displaying alarm information when the abnormality has occurred.

* * * * *